United States Patent
Sengenberger et al.

(10) Patent No.: US 11,730,374 B1
(45) Date of Patent: Aug. 22, 2023

(54) RADIO FREQUENCY APPLICATOR FOR A THERMOACOUSTIC IMAGING SYSTEM

(71) Applicant: ENDRA Life Sciences Inc., Ann Arbor, MI (US)

(72) Inventors: Jordan Sengenberger, Ann Arbor, MI (US); Christopher Nelson Davis, Ann Arbor, MI (US); Christopher Bull, Saline, MI (US); Charlton Chen, Northville, MI (US); Jang Hwan Cho, Ann Arbor, MI (US); Idan Steinberg, Superior Charter Township, MI (US); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 17/865,034

(22) Filed: Jul. 14, 2022

(51) Int. Cl.
 *A61B 5/00* (2006.01)
 *A61B 18/04* (2006.01)
 *A61B 8/08* (2006.01)
 *A61B 5/0507* (2021.01)
 *A61B 8/00* (2006.01)
 *A61B 5/05* (2021.01)

(52) U.S. Cl.
 CPC ............ *A61B 5/0093* (2013.01); *A61B 18/04* (2013.01); *A61B 5/0095* (2013.01); *A61B 5/05* (2013.01); *A61B 5/0507* (2013.01); *A61B 5/4244* (2013.01); *A61B 5/489* (2013.01); *A61B 8/00* (2013.01); *A61B 8/5261* (2013.01)

(58) Field of Classification Search
 CPC ....... A61B 5/0093; A61B 5/0095; A61B 5/05; A61B 5/0507; A61B 5/4244; A61B 5/489; A61B 18/04; A61B 8/00; A61B 8/5261
 See application file for complete search history.

(56) References Cited

U.S. PATENT DOCUMENTS

2021/0077018 A1* 3/2021 Cho .................... A61B 5/05
2021/0244384 A1* 8/2021 Barnes ............... A61B 8/4416

\* cited by examiner

*Primary Examiner* — Peter Luong
(74) *Attorney, Agent, or Firm* — Stanley E. Jelic (57) ABSTRACT

A radio frequency applicator for a thermoacoustic imaging system is disclosed. The applicator includes, a waveguide with an internal radio frequency source, wherein the waveguide has an opening, an electromagnetic matching layer coupled to the waveguide and proximate to the opening, and an acoustic absorbing layer that is coupled to the matching layer.

15 Claims, 9 Drawing Sheets

RADIO FREQUENCY APPLICATOR FOR A THERMOACOUSTIC IMAGING SYSTEM

TECHNICAL FIELD

This disclosure relates generally to thermoacoustic imaging, and more particularly to system and method for thermoacoustic imaging using a radio frequency applicator to preferentially condition received signals.

BACKGROUND

The statements in this section merely provide background information related to the present disclosure and may not constitute prior art.

In high frequency systems, it is common to employ waveguides to guide electromagnetic waves or sound with minimal loss of energy by restricting expansion of the electromagnetic waves propagating within the waveguides to one or two dimensions. Depending on the nature of the electromagnetic waves to be propagated, the waveguides may take different forms. In many instances, filters are employed to allow electromagnetic waves at some frequencies to pass and travel along the waveguides, while rejecting electromagnetic waves at other frequencies. For example, when propagating radio frequency (RF) waves, hollow, open-ended, conductive metal waveguides are often employed. In some instances, to provide the desired filtering, these hollow metal waveguides are fitted with a solid insert formed of high dielectric constant material.

Waveguides such as those described above have been employed in thermoacoustic imaging systems. Thermoacoustic imaging is an imaging modality that provides information relating to the thermoelastic properties of tissue. Thermoacoustic imaging uses short pulses of electromagnetic energy, such as RF pulses, directed into a subject to heat absorbing features within the subject rapidly, which in turn induces acoustic pressure waves that are detected using acoustic receivers such as one or more thermoacoustic or ultrasound transducer arrays. The detected acoustic pressure waves are analyzed through signal processing, and processed for presentation as thermoacoustic images that can be interpreted by an operator.

In order to direct RF pulses into the subject during thermoacoustic imaging, a radio frequency (RF) applicator employing a waveguide is coupled to tissue adjacent a region of interest (ROI) within the subject to be imaged. Sub-optimal coupling of the RF applicator to the tissue may cause issues such as inefficient energy transfer, reduced heating rates, reduced signal intensity, non-uniform energy deposition, tissue hotspots, tissue overheating, RF power supply damage, and poor image quality. Factors that lead to sub-optimal coupling of the RF applicator to the tissue include variability in the size of the subject, the size of tissue within the subject, the geometry of tissue within the subject, the composition of tissue within the subject, etc.

The strong electromagnetic field inside the applicator and in its closest vicinity (the top layers of the medium to be imaged) as well as the high conductivity of the skin layer generates a strong spurious acoustic wave close to the applicator's front face. This wave, which is of no clinical interest, propagates through the tissue and overshadows the desired thermoacoustic signals from various constituents, thus interfering with the measurement.

Many academic systems utilize a split-configuration where the applicator is either facing the acoustic sensor (opposed geometry) or at 90 degrees to the applicator (perpendicular geometry). Opposed geometry ensures that the interfering signal will arrive last and thus it is temporarily separated from the signals of interest. Perpendicular geometry configuration ensures that only a side-scattered wave will reach the detector and thus reduces the received interference greatly.

The shortcoming of both configurations however, is that those deviate greatly from the standard of care, since reflection-mode ultrasound requires separate handheld devices—applicator and detector. This will require considerable adaptation from the clinician, will be complicated to operate and will be very susceptible to the user's operation. Moreover, those geometries are many times impractical to perform on a clinical setting with a handheld and are more suited for full-body small animal imaging.

SUMMARY

A radio frequency applicator for a thermoacoustic imaging system is disclosed. The applicator includes: a waveguide with an internal radio frequency source, wherein the waveguide has an opening; an electromagnetic matching layer coupled to the waveguide and proximate to the opening; and an acoustic absorbing layer that is coupled to the matching layer.

In one embodiment, the electromagnetic matching layer, at a frequency range between 15 MHz and 2.5 GHz, has a real part of permittivity from 5 to 65 and an imaginary part of permittivity from 0 to 60.

In one embodiment, the electromagnetic matching layer, at a frequency range between 0.1 MHz and 20 GHz, has an acoustic impedance of greater than 3 MRayl.

In one embodiment, wherein the acoustic absorbing layer, at a frequency range between 15 MHz and 2.5 GHz, has a real part of permittivity from 5 to 65 and an imaginary part of permittivity from 0 to 60.

In one embodiment, the acoustic absorbing layer, at a frequency range between 0.1 MHz and 20 GHz, has an acoustic impedance between 1.2 MRayl and 1.8 MRayl.

In one embodiment, the electromagnetic matching layer, at a frequency range between 1 MHz and 1000 MHz, has a real part of permittivity from 2 to 80 and an imaginary part of permittivity from 0 to 60.

In one embodiment, the electromagnetic matching layer, at a frequency range between 0.01 Hz and 100 Hz, has an acoustic impedance of greater than 1 MRayl.

In one embodiment, the acoustic absorbing layer, at a frequency range between 1 MHz and 1000 MHz, has a real part of permittivity from 2 to 80 and an imaginary part of permittivity from 0 to 60.

In one embodiment, the acoustic absorbing layer, at a frequency range between 0.01 Hz and 100 Hz, has an acoustic impedance between 35 kRayl and 1 MRayl.

In one embodiment, the electromagnetic matching layer, at a frequency range between 3 kHz and 30 kHz, has a real part of permittivity from 2 to 100 and an imaginary part of permittivity from 0 to 60.

In one embodiment, the electromagnetic matching layer, at a frequency range between 50 kHz and 500 kHz, has an acoustic impedance of greater than 4 MRayl.

In one embodiment, the acoustic absorbing layer, at a frequency range between 3 kHz and 30 kHz, has a real part of permittivity from 2 to 100 and an imaginary part of permittivity from 0 to 60.

In one embodiment, at a frequency range between 50 kHz and 500 kHz, the acoustic absorbing layer has an acoustic impedance between 0.4 MRayl and 3 MRayl.

In one embodiment, the electromagnetic matching layer is formed of a high permittivity elastomer material.

In one embodiment, the electromagnetic matching layer is formed of a ceramic material.

In one embodiment, the electromagnetic matching layer is formed of a composite material which contain high permittivity particles embedded in a solid matrix.

In one embodiment, the acoustic absorbing layer is formed of an open-cell foam.

In one embodiment, the acoustic absorbing layer is formed of impregnated cork.

In one embodiment, the acoustic absorbing layer is formed of an acoustic anechoic absorber.

In one embodiment, the acoustic absorbing layer is formed of a rubber-based vibration isolation material.

This summary is provided merely to introduce certain concepts and not to identify key or essential features of the claimed subject matter.

BRIEF DESCRIPTION OF THE DRAWINGS

One or more embodiments will now be described, by way of example, with reference to the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment. The term "based upon" is not exclusive and allows for being based on additional factors not described, unless the context clearly dictates otherwise. Additionally, in the subject description, the word "exemplary" is used to mean serving as an example, instance or illustration.

Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientations depicted in the figures.

Reference herein to "example" means that one or more feature, structure, element, component, characteristic and/or operational step described in connection with the example is included in at least one embodiment and/or implementation of the subject matter according to the subject disclosure. Thus, the phrases "an example," "another example," and similar language throughout the subject disclosure may, but do not necessarily, refer to the same example. Further, the subject matter characterizing any one example may, but does not necessarily, include the subject matter characterizing any other example.

Reference herein to "configured" denotes an actual state of configuration that fundamentally ties the element or feature to the physical characteristics of the element or feature preceding the phrase "configured to".

Unless otherwise indicated, the terms "first," "second," etc. are used herein merely as labels, and are not intended to impose ordinal, positional, or hierarchical requirements on the items to which these terms refer. Moreover, reference to a "second" item does not require or preclude the existence of a lower-numbered item (e.g., a "first" item) and/or a higher-numbered item (e.g., a "third" item).

As used herein, the terms "approximately" and "about" represent an amount close to the stated amount that still performs the desired function or achieves the desired result. For example, the terms "approximately" and "about" may refer to an amount that is within engineering tolerances that would be readily appreciated by a person of ordinary skill in the art.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Figure 1:
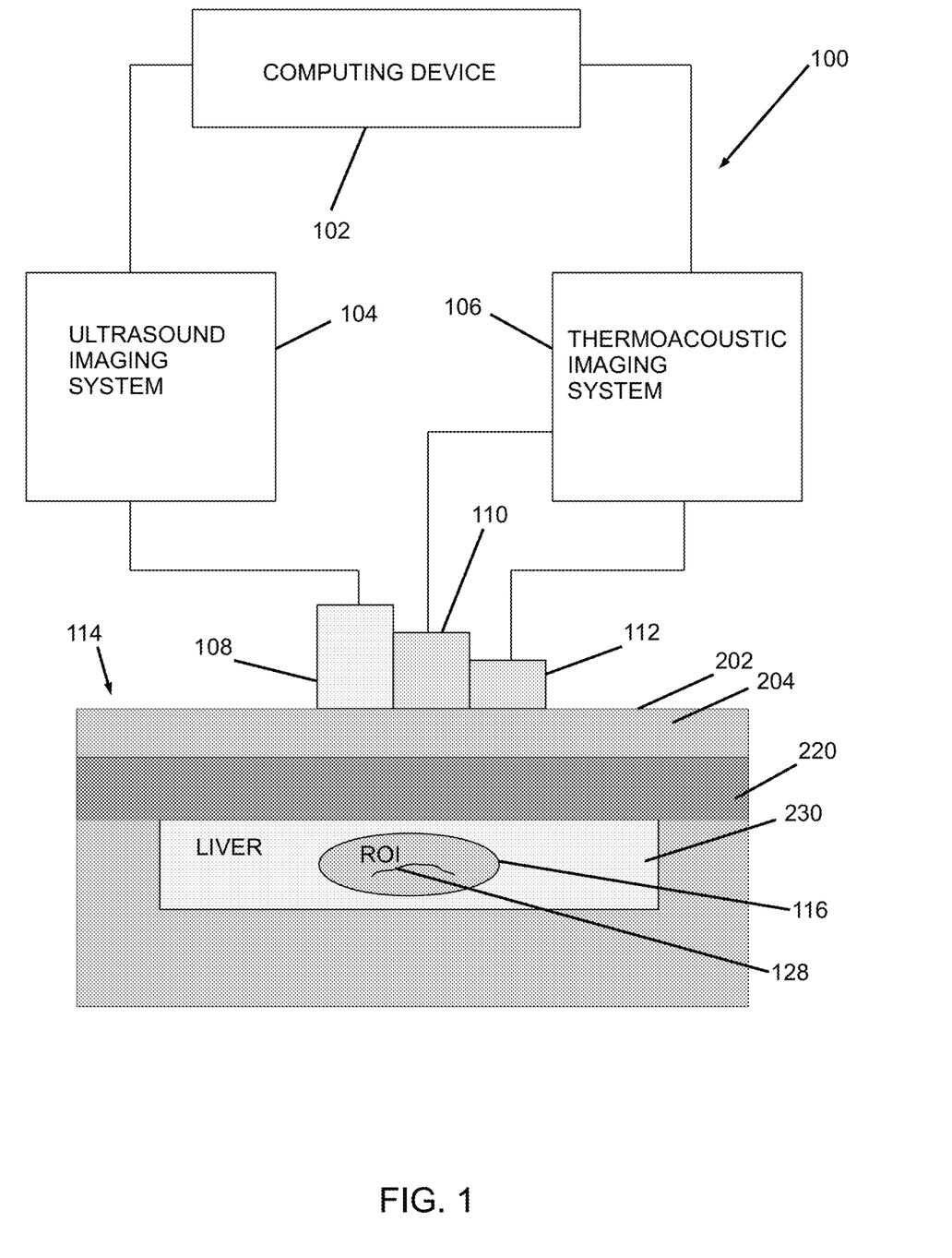
FIG. 1 schematically shows an exemplary imaging system and an exemplary region of interest in a liver with a blood vessel.

Referring now to the drawings, wherein the depictions are for the purpose of illustrating certain exemplary embodiments only and not for the purpose of limiting the same, FIG. 1 schematically shows an exemplary imaging system 100 is shown and is generally identified by reference numeral 100. As can be seen, the imaging system 100 includes a programmed computing device 102 communicatively coupled to an ultrasound imaging system 104 and to a thermoacoustic imaging system 106. The ultrasound imaging system 104 and thermoacoustic imaging system 106 are configured to obtain ultrasound image data and thermoacoustic image data, respectively, of a region of interest 116. Components of the system 100 are shown in FIG. 1 as single elements. Such illustration is for ease of description, and it should be recognized that the system 100 may include multiple additional imaging devices or sub-devices.

The programmed computing device 102 may be a computer, server or other suitable processing device comprising, for example, a processing unit comprising one or more processors, computer-readable system memory (volatile and/or non-volatile memory), other non-removable or removable computer-readable memory (e.g., a hard disk drive, RAM, ROM, EEPROM, CD-ROM, DVD, flash memory, etc.) and a system bus coupling the various computer components to the processing unit. The computing device 102 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 102 for receiving operator input. A display device (not shown), such as one or more computer screens or monitors, is coupled to the computing device 102 for displaying one or more generated images that are based on ultrasound image data received from the ultrasound imaging system 104 and/or the thermoacoustic image data received from thermoacoustic imaging system 106. The programmed computing device 102 executes program code stored on the computer-readable system memory and/or other non-removable or removable computer-readable memory and performs methods according to the program code as will be described further below.

The ultrasound imaging system 104 comprises an acoustic receiver in the form of an ultrasound transducer 108 that houses one or more ultrasound transducer arrays configured to emit sound waves into the region of interest 116. Sound waves directed into the region of interest 116 echo off materials within the region of interest ROI, with different materials reflecting varying degrees of sound. Echoes that are received by the one or more ultrasound transducer arrays of the ultrasound transducer 108 may be processed by the ultrasound imaging system 104 before being communicated as ultrasound image data to the computing device 102 for further processing and for presentation on the display device as ultrasound images that can be interpreted by an operator. In one embodiment, the ultrasound imaging system 104 utilizes B-mode ultrasound imaging techniques assuming a nominal speed of sound of 1,540 m/s. As ultrasound imaging systems are known in the art, further specifics of the ultrasound imaging system 104 will not be described further herein.

The thermoacoustic imaging system 106 comprises an acoustic receiver in the form of a thermoacoustic transducer 110. The thermoacoustic transducer 110 houses one or more thermoacoustic transducer arrays. Radio-frequency (RF) applicator 112 may be housed together or separately from the thermoacoustic transducer 110. The RF applicator 112 is configured to emit short pulses of RF energy that are directed into the region of interest ROI, which contains blood vessel 128. In one embodiment, the RF applicator 112 has a frequency between about 10 Mhz and 100 GHz and has a pulse duration between about 0.1 nanoseconds and 10 microseconds. RF energy pulses delivered to materials within the region of interest 116 induce acoustic pressure waves (thermoacoustic multi-polar signals) within the region of interest 116 that are detected by the thermoacoustic transducer 110. Acoustic pressure waves that are detected by the thermoacoustic transducer 110 are processed and communicated as thermoacoustic image data to the computing device 102 for further processing and for presentation on the display device as thermoacoustic images that can be interpreted by the operator.

The coordinate system of the one or more ultrasound transducer arrays of the ultrasound transducer 108 and the coordinate system of the one or more thermoacoustic transducer arrays of the thermoacoustic transducer 110 are mapped by the computing device 102 so that acquired ultrasound and thermoacoustic images can be registered. Alternatively, the thermoacoustic imaging system 106 may make use of the one or more ultrasound transducer arrays of the ultrasound transducer 108 by disconnecting the one or more ultrasound transducer arrays from the ultrasound transducer 108 and connecting the one or more ultrasound transducer arrays to the thermoacoustic transducer 110. As will be appreciated, by doing this coordinate mapping between the one or more ultrasound transducer arrays and the one or more thermoacoustic transducer arrays is not required.

In one embodiment (shown in FIG. 1), an exemplary region of interest 116 contains a blood vessel 128 and is located within a liver 230 of a human or animal body (patient) 114. Patient 114 comprises a skin 202 and subcutaneous fat layer 218 and muscle layer 220 adjacent to liver 230.

In one embodiment, a radio-frequency (RF) applicator 112 comprises a waveguide with an internal radio frequency source, wherein the waveguide has an opening. In various embodiments, a waveguide comprises an antenna and applicator, and/or components configured to transfer RF and/or microwave energy into tissue.

Figure 2:
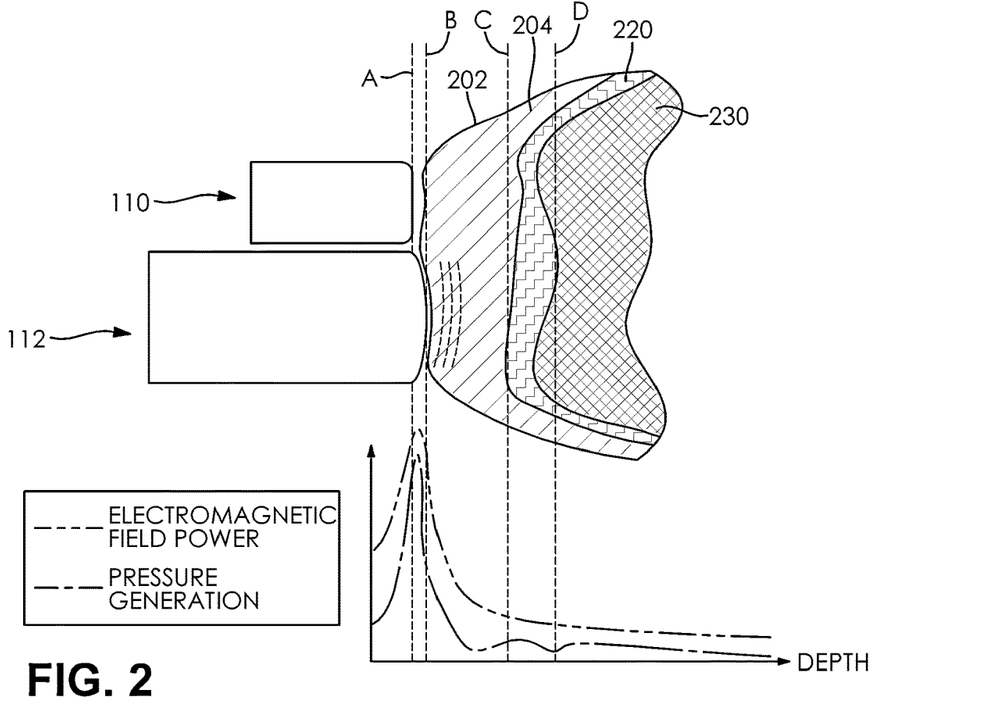
FIG. 2 shows an exemplary side-view of a thermoacoustic application.

FIG. 2 shows an exemplary RF applicator 112 and thermoacoustic transducer 110 in an exemplary application. As FIG. 2 shows, skin 202, fat (including subcutaneous fat) 204, muscle 220, and liver (or another organ) 230 are present in a patient. Thermoacoustic signals are generated at the interfaces between the RF applicator 112 and skin 202 (shown in FIG. 2 as line 'A'), skin 202 and fat 204 (shown in FIG. 2 as line 'B'), fat 204 and muscle 220 (shown in FIG. 2 as line 'C'), and muscle 220 and liver 230 (shown in FIG. 2 as line 'D'). The thermoacoustic signals generated at the interfaces between the RF applicator 112 and skin 202 and the skin 202 and fat 204 (e.g., lines A and B shown in FIG. 2) are not desirable and can interfere with thermoacoustic signals generated at the interfaces between fat 204 and muscle 220, and muscle 220 and liver 230. Hence, the present disclosure describes embodiments configured to minimize thermoacoustic signal strength (amplitude) generated at the interfaces between the RF applicator 112 and skin 202 and the skin 202 and fat 204, while maximizing signal strength (amplitude) generated at the interfaces between fat 204 and muscle 220, and muscle 220 and liver 230 (e.g., interference lines C and D of FIG. 2). These embodiments are novel RF applicator 112 configurations.

Figure 3:
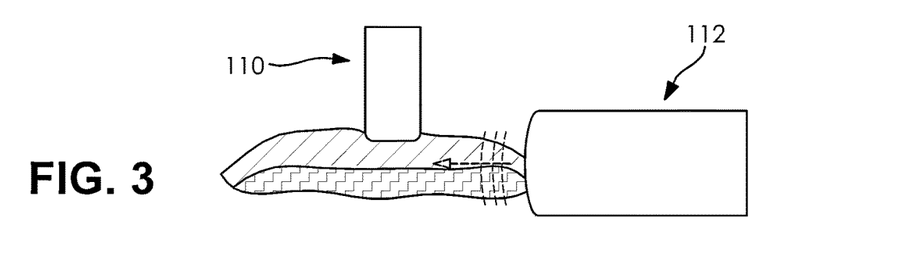
FIG. 3 shows an exemplary split configuration thermoacoustic system.

FIG. 3 shows a split configuration (perpendicular geometry) embodiment of the thermoacoustic transducer 110 and the RF applicator 112 of the system 100. Perpendicular geometry configuration ensures that only a side-scattered wave will reach the detector and thus reduces the received interference greatly. In some embodiments, the RF applicator 112 is disposed at angles that are substantially 90-degrees from the thermoacoustic transducer 110, e.g., 75-115-degrees, from the thermoacoustic transducer 110.

Figure 4:
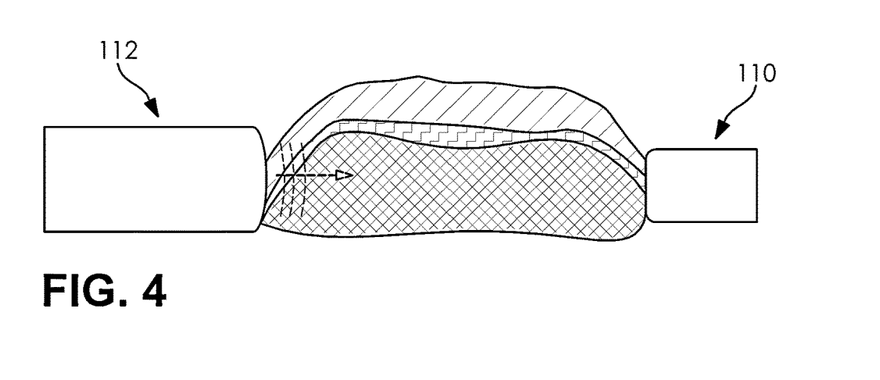
FIG. 4 shows an exemplary opposed geometry thermoacoustic system.

FIG. 4 shows an opposed geometry embodiment of the thermoacoustic transducer 110 and the RF applicator 112 of the system 100. Opposed geometry ensures that the interfering signal will arrive last and thus it is temporarily separated from the signals of interest.

Figure 5:
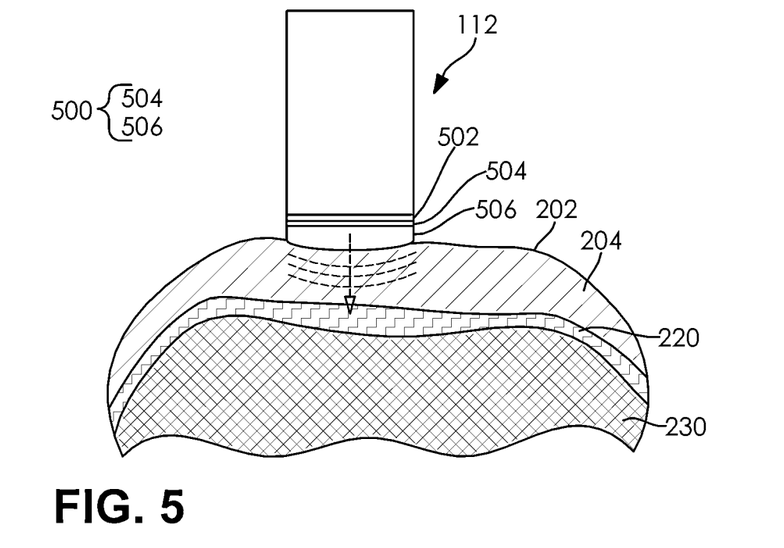
FIG. 5 shows a cross-sectional side view of a radio-frequency applicator embodiment.

FIG. 5 shows an exemplary cross-sectional side view of a radio-frequency applicator 112 having an acoustic absorption layer 500. Shown are RF applicator 112, skin 202, fat 204, muscle 220, liver 230, electromagnetic matching layer 502, cloth layer 504, and foam layer 506. In one embodiment, the acoustic absorption layer 500 includes the cloth layer 504 and the foam layer 506. In one embodiment, the RF applicator 112 is preconfigured with electromagnetic matching layer 502. In one embodiment, the electromagnetic matching layer 502 is integral with the applicator 112. In one embodiment, the electromagnetic matching layer 502 is coupled to the applicator via, e.g., adhesive. In one embodiment, the electromagnetic matching layer 502 is coupled to the insert 1010. As FIG. 5 shows, thermoacoustic signals are reduced and absorbed by material in the acoustic absorption layer 500 (shown in FIG. 6 as line 'E').

Figure 6:
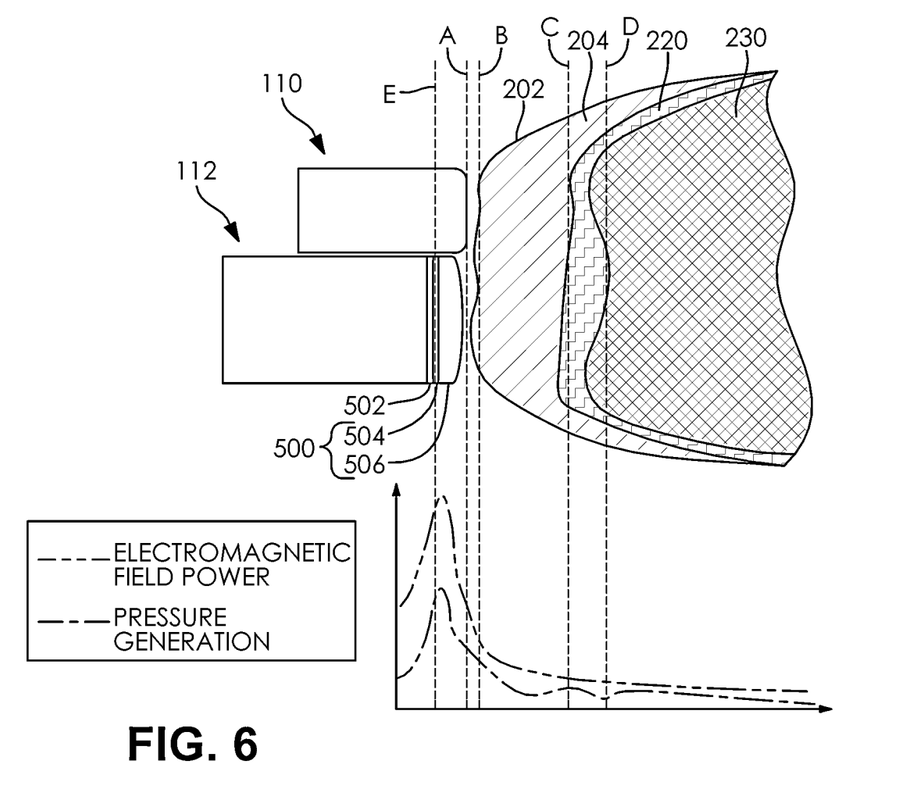
FIG. 6 shows a cross-sectional side view of a thermoacoustic application embodiment.

FIG. 6 shows a cross-sectional side view of an embodiment of the thermoacoustic transducer 110 and the RF applicator 112 of the system 100. Shown are the RF applicator 112 and the thermoacoustic transducer 110 a patient having skin 202, fat 204, muscle 220, liver 230. The RF applicator 112 includes an electromagnetic matching layer 502, cloth layer 504, and foam layer 506. In one embodiment, cloth layer 504 and foam layer 506 comprise an acoustic absorption layer 500.

The electromagnetic matching layer 502 is preferably configured to substantially match the electrical impedance of a target material, e.g., tissue, while not matching the acoustic impedance of the target, e.g., the tissue. The target material can include one or more of: the skin 202, the subcutaneous fat layer 218, the muscle layer 220, and the liver 230.

Cloth layer 504 preferably substantially matches the electrical and acoustic characteristics of the electromagnetic matching layer 502, while serving to connect the electromagnetic matching layer 502 with the foam layer 506. Foam layer 506, is preferably configured to substantially match both the electrical impedance of tissue and the acoustic impedance of tissue. Hence, the combination of electromagnetic matching layer 502, cloth layer 504, and foam layer 506 minimizes acoustic transfer from the RF applicator 112, maximizes RF energy transfer to tissue (e.g., the skin layer 202), and captures and disperses spurious, i.e., undesired, signals generated at the RF applicator 112 and skin 202 interface (shown in FIG. 6 as line 'A'), and the skin 202 and fat 204 interface (shown in FIG. 6 as line 'B'). The shape of the acoustic absorption layer 500, in particular the foam layer 506, helps to further disperse unwanted acoustic signals that could interfere with signals emanating from desired imaging regions (e.g., the ROI as shown in FIG. 1) and from interference lines 'C' and 'D' of FIG. 6.

In various embodiments, the acoustic absorption layer 500 includes a saline-soaked open foam layer 506 with a cloth backing 504. The cloth 504 can have an adhesive layer that allows sticking (either permanently or temporarily, in various embodiments) it on top of the applicator 112. The acoustic absorption layer 500 can mitigate the generated spurious acoustic waves by: A) having strong acoustic scattering and/or absorption that mitigates the wave generated at the interface between the layer 500 and the applicator 112 from propagating further into the tissue; B) enforces a standoff between the tissue (e.g., skin 202 and/or fat 204) and the applicator 112. As the electromagnetic field peaks near the applicator 112 front face—this standoff reduces the electromagnetic field that reaches the highly conductive skin layer; C) Acts as an acoustic matched layer boundary around the applicator 112 and thus reduces strong acoustic reflections from this region; D) In one embodiment, the layer 500 is shaped to deflect signals away from the shortest perpendicular location from the RF emitter 110.

In one embodiment, the absorption layer 500 has a cross-section of the shape is an arrow shape with an angle varying from 0-60 degrees and the vertex centered. In one embodiment, portions of the absorption layer 500 have a conical-shape or a partial conical-shape. In various embodiments, the absorption layer 500 includes portions having a frustal-conical shape, a pyramidal shape, frustum-pyramidal shape, or a parallelepiped shape.

Embodiments of the system 100 having an RF applicator 112 with acoustic absorption layer 500 provides: (1) mitigation of spurious signals; and (2) the use of a single supplementary layer to address both the signal generated at the applicator's 112 surface and the skin surface from both electrical (through standoff) and acoustic (through matching and absorbing).

In various embodiments, a similar layer can also be applicable to photoacoustic imaging. i.e., to match the refractive index of tissue while being acoustically absorbing will reduce the spurious acoustic wave at the interface.

In various embodiments, the cloth backing 504 and adhesive layer are not necessary and can be replaced or removed. Shaping of the layer is also not necessary.

In various embodiments, the RF applicator 112 includes a waveguide 702 with an internal radio frequency source 1018. The waveguide preferably has an opening 1016. The acoustic absorption layer 500 is sized and shaped to cover the opening 1016.

In one embodiment, the foam layer 506 has a minimum thickness of 5 millimeters and a maximum thickness of 15 millimeters.

Figure 7:
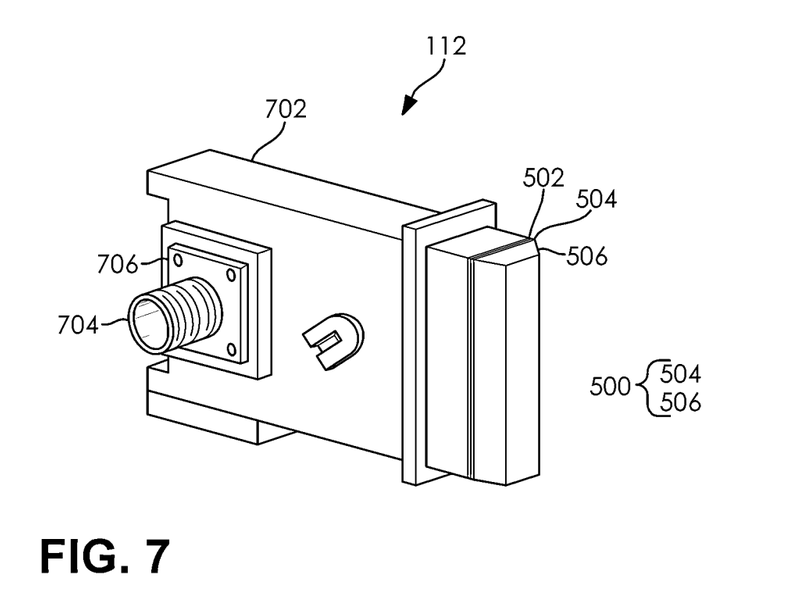
FIG. 7 shows a perspective view of an exemplary radio-frequency applicator.

FIG. 7 shows a perspective view of an exemplary radio-frequency applicator 112 embodiment. As FIG. 7 shows, the RF applicator 112 can include a RF waveguide 702, electromagnetic matching layer 502, cloth layer 504, and foam layer 506, which comprise an acoustic absorption layer 500. The exemplary acoustic absorption layer 500 is shown with tapered edges on the foam layer 506.

Figure 8A:
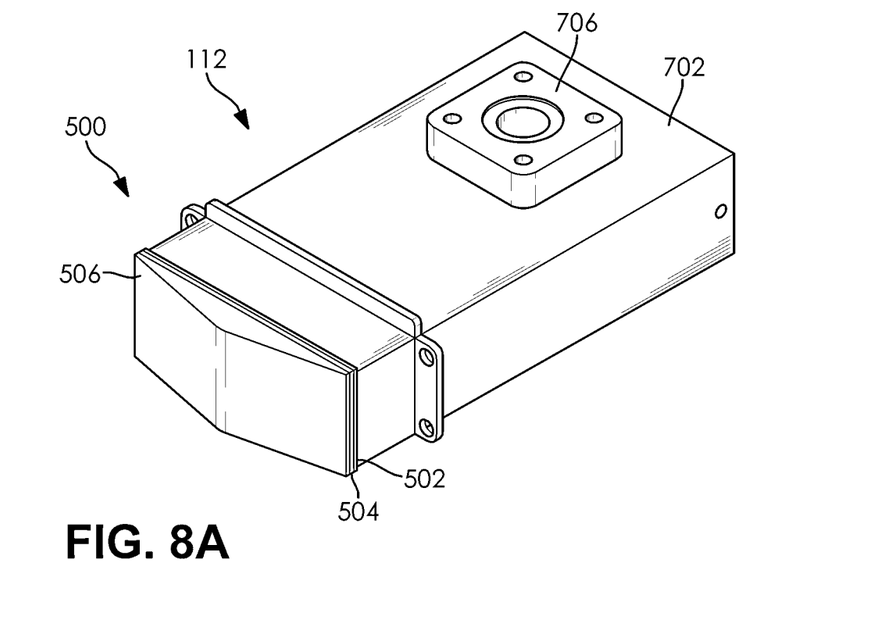
FIGS. 8A and 8B shows perspective views of another exemplary radio-frequency applicator.
Figure 8B:
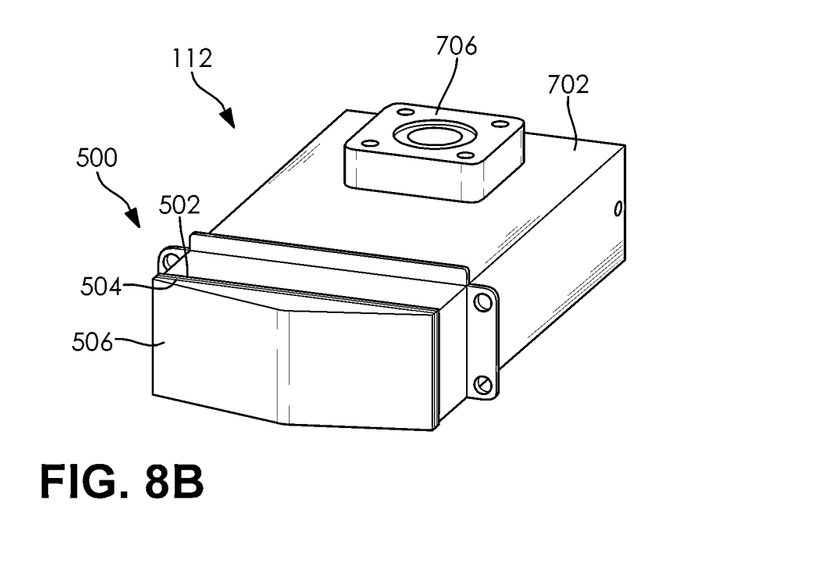

FIGS. 8A and 8B show another radio-frequency applicator embodiment illustrating an exemplary shape of the acoustic absorption layer 500. As FIGS. 8A and 8B show, the acoustic absorption layer 500 has tapered sides leading to a central edge, i.e., a lined vertex, on the leading surface. In this embodiment, the acoustic absorption layer 500 has an arrow cross-sectional shape.

Figure 9A:
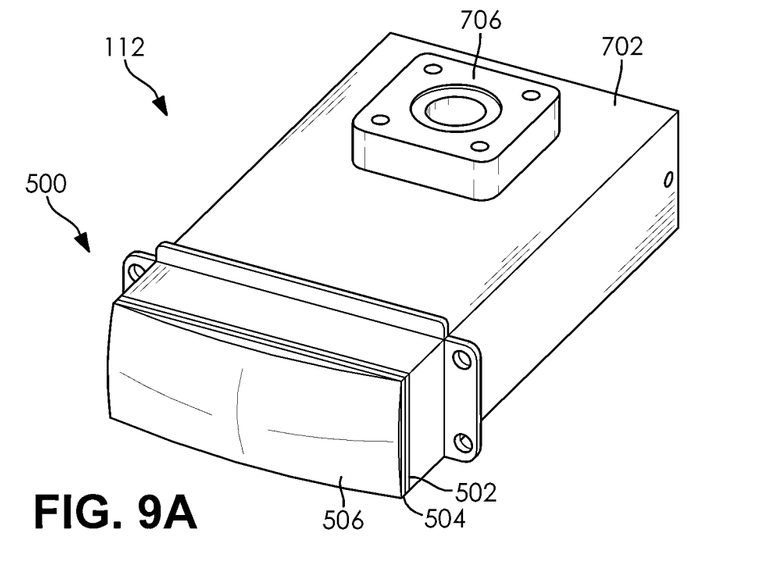
FIGS. 9A and 9B shows perspective views of another exemplary radio-frequency applicator.
Figure 9B:
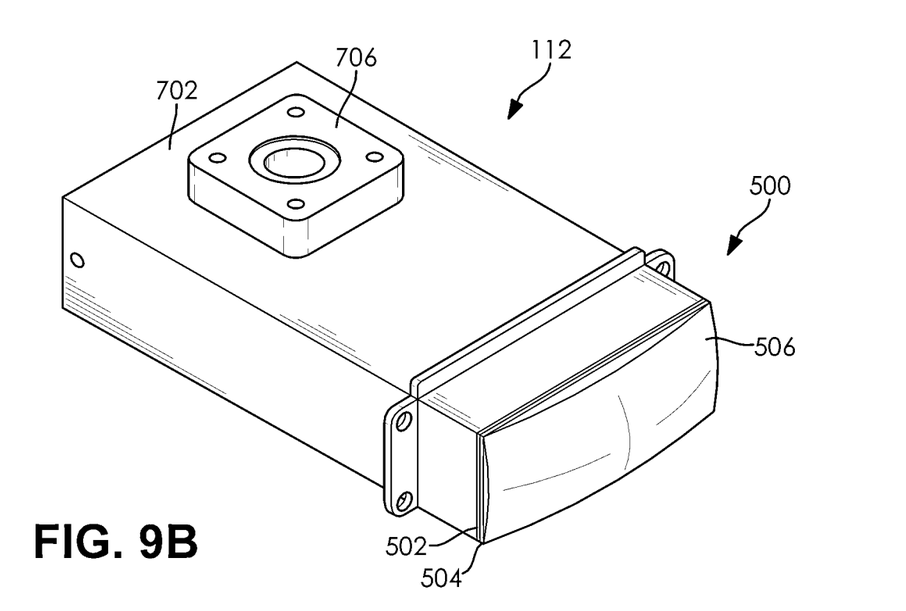

FIGS. 9A and 9B show another radio-frequency applicator embodiment illustrating an exemplary shape of the acoustic absorption layer 500. As FIGS. 9A and 9B show, the acoustic absorption layer 500 has a rounded leading surface, i.e., a bulged central vertex. It is contemplated herein that other embodiments having a vertex in a central region of a leading surface of the acoustic absorption layer 500 similar to the embodiment of FIGS. 9A and 9B may be used.

Figure 10:
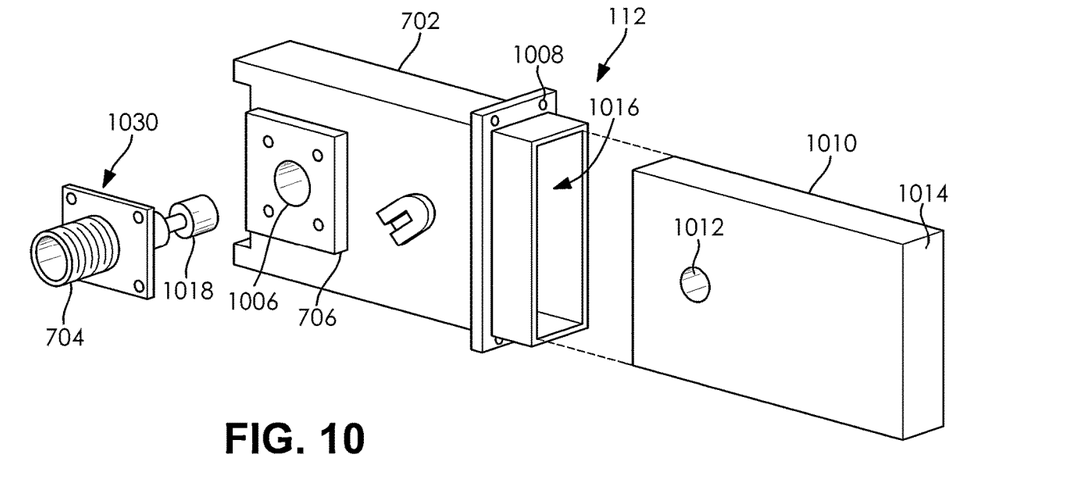
FIG. 10 shows another exemplary radio-frequency applicator.

FIG. 10 shows a perspective view of another exemplary radio-frequency applicator 112. As can be seen, the RF applicator 112 comprises a hollow, generally rectangular, open-ended waveguide 702, which can be formed of electrically conductive metal material. A plinth 706 is provided on a surface of the waveguide 702 adjacent one end thereof. A central aperture 1006 is provided in the plinth 706 and extends through the surface of the waveguide 702. A flange 1008 can extend about the waveguide 702 adjacent the other end thereof and can be utilized to mount the RF applicator 112 within a thermoacoustic probe which includes thermoacoustic transducer 110 and may include ultrasound transducer 108.

A solid, low loss, high dielectric constant insert 1010 formed of ceramic or other suitable material is positioned within the interior of the waveguide 702 and can fill the internal volume of the waveguide 702. A recess 1012 is provided in the high dielectric constant insert 1010 that is aligned with the aperture 1006. In one embodiment, high dielectric constant refers to a real relative permittivity greater than 10 and low loss refers to a loss tangent less than 0.01.

Insert 1010 has a surface facing 1014 which lies substantially flush with waveguide opening 1016. The opening 1016 is configured for electromagnetic energy communication therethrough. The opening 1016 is rectangular-shaped, but various sizes and shapes of the opening may be used in various embodiments, consistent with the opening being configured for electromagnetic energy communication therethrough.

An RF source 1030 having an RF emitter 1018 at one end that is configured to generate RF energy pulses, extends through the aperture 1006 and into waveguide 702 so that the RF emitter 1018 is suspended within waveguide 702. The RF source 1030 further includes a threaded connector 704 to which control electronics may be connected. In one embodiment, the RF source 1030 is configured to engage the plinth 706 and through which threaded fasteners pass. A mounting flange 1030 that overlies the plinth 706 to secure the RF emitter 1018 within the waveguide 702. The RF emitter 1018 functions as an internal radio frequency source for the waveguide 702.

In one embodiment, which may be desirable in medical applications that enable thermoacoustic measurements in tissue, the electromagnetic matching layer 502 has the following electromagnetic properties at a target frequency range between 15 MHz and 2.5 GHz: A) a real part of permittivity in a range from 5 to 65; and B) an imaginary part of the permittivity in a range 0 to 60.

For various applications, such as medical applications, the electromagnetic matching layer 502 may have the following acoustic properties at a target frequency range between 0.1 MHz and 20 GHz: A) a speed of sound greater than 2000 m/s; B) a density greater than 1500 kg/m^3; and C) an acoustic impedance greater than 3 MRayl (acoustic impedance is the speed of sound times the density).

For various applications, such as medical applications, the electromagnetic matching layer 502 can be formed of high permittivity elastomers (e.g., Avient's Preperm®), ceramics (e.g., National Magnetics' k-60®), and/or composite materials which contain high-permittivity particles embedded in a solid matrix (e.g., PPG's Des-K®).

For various applications, such as medical applications, the acoustic absorption layer 500, can have the following electromagnetic properties at the target frequency range between 15 MHz and 2.5 GHz: A) a real part of permittivity in a range from 5 to 65; and B) an imaginary part of permittivity in a range from 0 to 60.

For various applications, such as medical applications, the acoustic absorption layer 500, can have the following acoustic properties at a target frequency range between 0.1 MHz and 20 GHz: A) An acoustic attenuation from 0.3 dB/(cm*MHz) to 30 dB/(cm*MHz); B) a speed of sound between 1350 and 1650 m/s; C) a density between 900 and 1100 kg/m^3; and D) an acoustic impedance from 1.2 to 1.8 MRayl, which is close to tissue (1.5 MRayl) (acoustic impedance is the speed of sound times the density).

The acoustic absorption layer 500 may be formed of open-cell foams, since foam has high acoustic attenuation. In a separate embodiment, an open-cell foam can be soaked with saline or other another liquid to modify its acoustic and electro-magnetic properties to match the cited ranges of this disclosure.

In one embodiment, the acoustic absorption layer 500 is formed of impregnated cork, wherein particles used for impregnating it are chosen in such a manner they tune the cork to match the cited ranges of this disclosure. In one embodiment, the acoustic absorption layer 500 is commercially available acoustic anechoic absorber (e.g., Precision acoustics' Aptflex®).

In one embodiment, which may be desirable in ground-penetrating thermoacoustic measurements, the electromagnetic matching layer 502 can have the following electromagnetic properties at a target frequency range between 1 MHz and 1000 MHz: A) a real part of permittivity in a range from 2 to 80; and B) an imaginary part of the permittivity in a range 0 to 60.

For various applications, such as ground-penetrating thermoacoustic applications, the electromagnetic matching layer 502 can have the following acoustic properties at a target frequency range between 0.01 MHz and 100 GHz: A) a speed of sound greater than 500 m/s; B) a density greater than 2000 kg/m^3; and C) an acoustic impedance greater than 1 MRayl (acoustic impedance is the speed of sound times the density).

For various applications, such as ground-penetrating thermoacoustic applications, it may be desirable for the electromagnetic matching layer 502 to be formed of high permittivity elastomers (e.g., Avient's Preperm®), ceramics (e.g., National Magnetics' k-60®), and/or composite materials which contain high-permittivity particles embedded in a solid matrix (e.g., PPG's Des-K®).

For various applications, such as ground-penetrating thermoacoustic applications, the acoustic absorption layer 500, may have the following electromagnetic properties at the target frequency range between 1 MHz and 1000 MHz: A) a real part of permittivity in a range from 2 to 80; and B) an imaginary part of permittivity in a range from 0 to 60.

The acoustic absorption layer 500, may have the following acoustic properties at a target frequency range between 0.01 Hz and 100 Hz: A) An acoustic attenuation of greater than 1 dB/(cm*kHz); B) a speed of sound between 70 and 700 m/s; C) a density between 500 and 1500 kg/m^3; and D) an acoustic impedance should from 35 kRayl to 1 MRayl, (acoustic impedance is the speed of sound times the density).

The acoustic absorption layer 500 can be formed of various materials including Sorbothane® and/or other rubber-based vibration isolation materials such as Neoprene® and Nitrile®.

In one embodiment, which may be desirable for making underwater thermoacoustic measurements, the electromagnetic matching layer 502 has the following electromagnetic properties at a target frequency range between 3 kHz and 30 kHz: A) a real part of permittivity in a range from 2 to 100; and B) an imaginary part of the permittivity in a range 0 to 60.

For various applications, such as underwater thermoacoustic applications, the electromagnetic matching layer 502 has the following acoustic properties at a target frequency range between 50 kHz and 500 kHz: A) a speed of sound greater than 2000 m/s; B) a density greater than 2000 kg/m^3; and C) an acoustic impedance greater than 4 MRayl (acoustic impedance is the speed of sound times the density).

For various applications, such as underwater thermoacoustic applications, it may be desirable for the electromagnetic matching layer 502 to be formed of high permittivity elastomers (e.g., Avient's Preperm®), ceramics (e.g., National Magnetics' k-60®), and/or composite materials which contain high-permittivity particles embedded in a solid matrix (e.g., PPG's Des-K®).

For various applications, such as underwater thermoacoustic applications, the acoustic absorption layer 500, can have the following electromagnetic properties at the target frequency range between 3 kHz and 30 kHz: A) a real part of permittivity in a range from 2 to 100; and B) an imaginary part of permittivity in a range from 0 to 60.

The acoustic absorption layer 500, can have the following acoustic properties at a target frequency range between 50 kHz and 500 kHz: A) An acoustic attenuation from 3 dB/(cm*MHz) to 50 dB/(cm*MHz); B) a speed of sound between 80 and 2000 m/s; C) a density between 500 and 1500 kg/m^3; and D) an acoustic impedance should from 0.4 MRayl to 3 MRayl, (acoustic impedance is the speed of sound times the density).

For various applications, such as underwater thermoacoustic applications, it may be desirable for the acoustic absorption layer 500 to be formed of Sorbothane® material, and/or other rubber-based vibration isolation materials such as Neoprene® and Nitrile®, and high-density cork.

Figure 11:
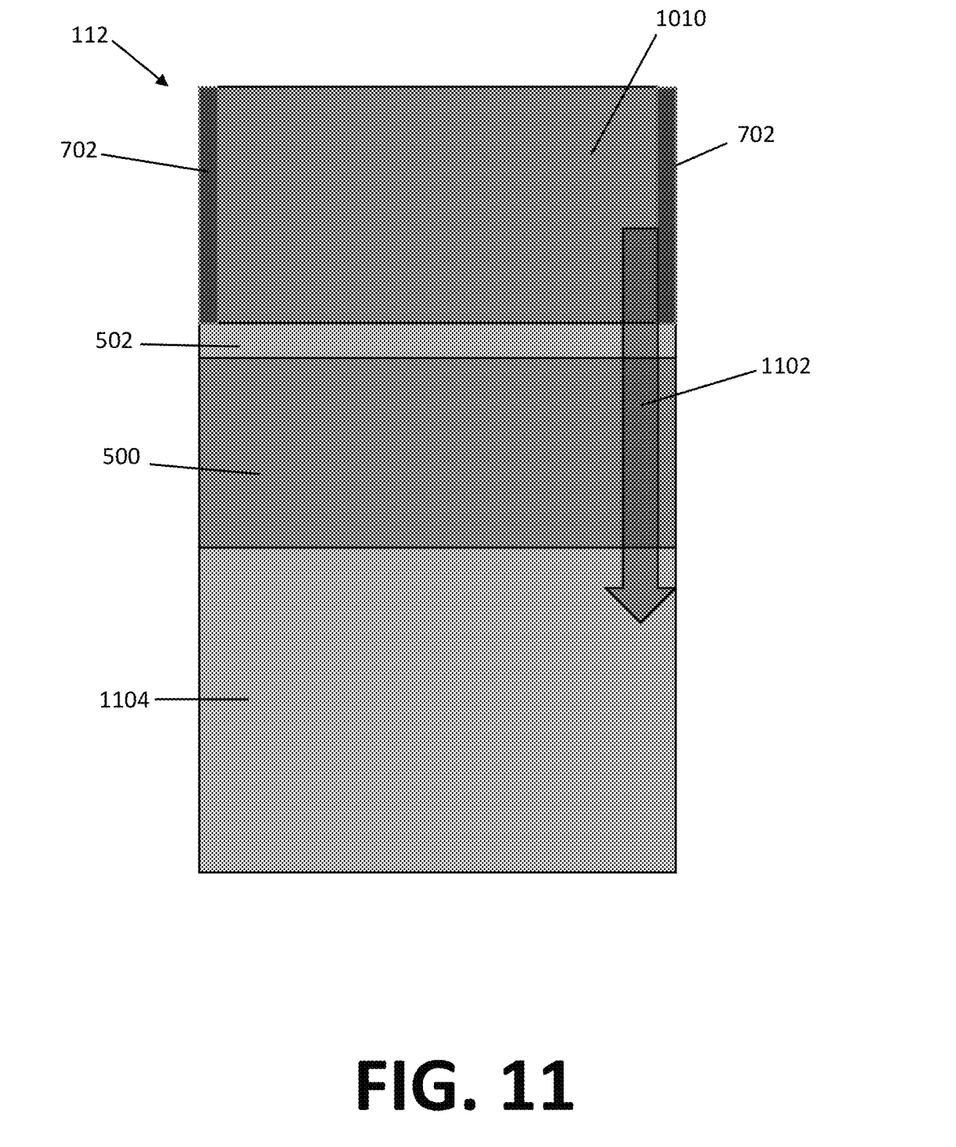
FIG. 11 schematically shows exemplary radio-frequency applicator, illustrating a directional flow of electro-magnetic energy.

FIG. 11 schematically shows a cross-sectional side view of an embodiment to illustrate a directional flow of electromagnetic energy during use. RF energy 1102 is shown being emitted from RF applicator 112 and passing first through electromagnetic matching layer 502, then acoustic absorption layer 500, and then being absorbed in measured media 1104. The measured media 1104 can be tissue (medical applications), ground (earth, ground-penetrating applications), or freshwater or saltwater (underwater thermoacoustics).

Figure 12:
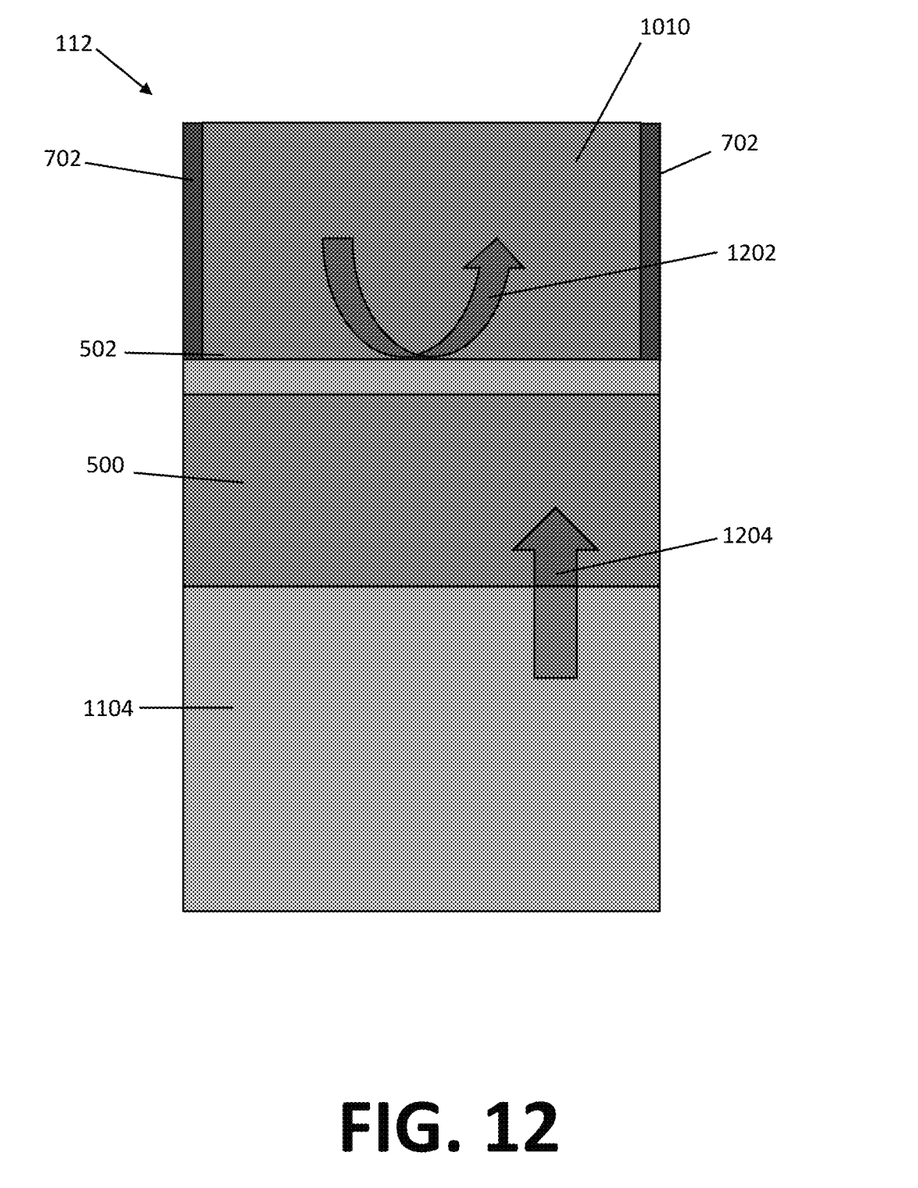
FIG. 12 schematically shows exemplary radio-frequency applicator, illustrating a directional flow of acoustic signal (acoustic energy).

FIG. 12 schematically shows a cross-sectional side view of an embodiment to illustrate a directional flow of acoustic signal (acoustic energy). The RF applicator 112 emits unwanted RF applicator acoustic energy 1202, which is reflected back from electromagnetic matching layer 502. Additionally, acoustic absorption layer 500 absorbs unwanted tissue acoustic energy 1204 emanating from tissue 1104. The measured media 1104 can be tissue (medical applications), ground (earth, ground-penetrating applications), or freshwater or saltwater (underwater thermoacoustics).

While the foregoing disclosure discusses illustrative embodiments, it should be noted that various changes and modifications could be made herein without departing from the scope of the described embodiments as defined by the appended claims. Accordingly, the described embodiments are intended to embrace all such alterations, modifications and variations that fall within scope of the appended claims. Furthermore, although elements of the described embodiments may be described or claimed in the singular, the plural is contemplated unless limitation to the singular is explicitly stated. Additionally, all or a portion of any embodiment may be utilized with all or a portion of any other embodiments, unless stated otherwise.

We claim:

1. A radio frequency applicator for a thermoacoustic imaging system, the applicator comprising:
a waveguide with an internal radio frequency source, wherein the waveguide has an opening;
an electromagnetic matching layer coupled to the waveguide and proximate to the opening; and
an acoustic absorbing layer that is coupled to the matching layer.

2. The radio frequency applicator of claim 1, wherein the electromagnetic matching layer, at a frequency range between 15 MHz and 2.5 GHz, has a real part of permittivity from 5 to 65 and an imaginary part of permittivity from 0 to 60.

3. The radio frequency applicator of claim 1, wherein the acoustic absorbing layer, at a frequency range between 15 MHz and 2.5 GHz, has a real part of permittivity from 5 to 65 and an imaginary part of permittivity from 0 to 60.

4. The radio frequency applicator of claim 1, wherein the acoustic absorbing layer, at a frequency range between 0.1 MHz and 20 GHz, has an acoustic impedance between 1.2 MRayl and 1.8 MRayl.

5. The radio frequency applicator of claim 1, wherein the electromagnetic matching layer, at a frequency range between 1 MHz and 1000 MHz, has a real part of permittivity from 2 to 80 and an imaginary part of permittivity from 0 to 60.

6. The radio frequency applicator of claim 1, wherein the acoustic absorbing layer, at a frequency range between 1 MHz and 1000 MHz, has a real part of permittivity from 2 to 80 and an imaginary part of permittivity from 0 to 60.

7. The radio frequency applicator of claim 1, wherein the acoustic absorbing layer, at a frequency range between 0.01 Hz and 100 Hz, has an acoustic impedance between 35 kRayl and 1 MRayl.

8. The radio frequency applicator of claim 1, wherein the electromagnetic matching layer, at a frequency range between 3 kHz and 30 kHz, has a real part of permittivity from 2 to 100 and an imaginary part of permittivity from 0 to 60.

9. The radio frequency applicator of claim 1, wherein the acoustic absorbing layer, at a frequency range between 3 kHz and 30 kHz, has a real part of permittivity from 2 to 100 and an imaginary part of permittivity from 0 to 60.

10. The radio frequency applicator of claim 1, wherein at a frequency range between 50 kHz and 500 kHz, the acoustic absorbing layer has an acoustic impedance between 0.4 MRayl and 3 MRayl.

11. The radio frequency applicator of claim 1, wherein the electromagnetic matching layer is formed of a ceramic material.

12. The radio frequency applicator of claim 1, wherein the acoustic absorbing layer is formed of an open-cell foam.

13. The radio frequency applicator of claim 1, wherein the acoustic absorbing layer is formed of impregnated cork.

14. The radio frequency applicator of claim 1, wherein the acoustic absorbing layer is formed of an acoustic anechoic absorber.

15. The radio frequency applicator of claim 1, wherein the acoustic absorbing layer is formed of a rubber-based vibration isolation material.

\* \* \* \* \*